United States Patent
Hofenk et al.

(10) Patent No.: US 12,188,032 B2
(45) Date of Patent: Jan. 7, 2025

(54) TRANSCRIPTION FACTOR-MEDIATED PROMOTION OF DIRECT SOMATIC EMBRYOGENESIS

(71) Applicant: PERPETUUM CROPSCIENCE BVBA, Antwerp (BE)

(72) Inventors: Jeroen Hofenk, Antwerp (BE); James Troch, Antwerp (BE)

(73) Assignee: PERPETUUM CROPSCIENCE BV, Antwerp (BE)

( * ) Notice: Subject to any disclaimer, the term of this patent is extended or adjusted under 35 U.S.C. 154(b) by 429 days.

(21) Appl. No.: 17/437,741

(22) PCT Filed: Mar. 11, 2020

(86) PCT No.: PCT/EP2020/056457
§ 371 (c)(1),
(2) Date: Sep. 9, 2021

(87) PCT Pub. No.: WO2020/182857
PCT Pub. Date: Sep. 17, 2020

(65) Prior Publication Data
US 2022/0144900 A1   May 12, 2022

(30) Foreign Application Priority Data
Mar. 12, 2019 (EP) .................... 19162059

(51) Int. Cl.
*C12N 15/82* (2006.01)
*A01H 4/00* (2006.01)
*C07K 14/415* (2006.01)

(52) U.S. Cl.
CPC ......... *C12N 15/8262* (2013.01); *A01H 4/002* (2021.01); *A01H 4/005* (2013.01); *C07K 14/415* (2013.01); *C07K 2319/033* (2013.01); *C07K 2319/09* (2013.01)

(58) Field of Classification Search
CPC .... C12N 15/8262; A01H 4/002; A01H 4/005; C07K 14/415; C07K 2319/033; C07K 2319/09
See application file for complete search history.

(56) References Cited

U.S. PATENT DOCUMENTS

| | | | |
|---|---|---|---|
| 6,921,848 B2* | 7/2005 | Chory | C07K 14/415 536/23.6 |
| 2003/0150026 A1 | 8/2003 | Chory et al. | |
| 2016/0286749 A1 | 10/2016 | Garcia Rojas et al. | |

OTHER PUBLICATIONS

Li, Qian-Feng et al. "The brassinosteroid-regulated transcription factors BZR1/BES1 function as a coordinator in multisignal-regulated plant growth." Biochimica et biophysica acta. Gene regulatory mechanisms vol. 1861,6 (2018): 561-571. doi: 10.1016/j.bbagrm.2018.04.003 (Year: 2018).*

(Continued)

*Primary Examiner* — Charles Logsdon
*Assistant Examiner* — Kelsey L McWilliams
(74) *Attorney, Agent, or Firm* — Workman Nydegger

(57) ABSTRACT

A recombinant protein for use in a liquid culture medium for photo-autotrophic micropropagation of *Cannabis sativa* L. is disclosed. The recombinant protein comprises a fusion of a growth induction part and a uptake enhancement part. The growth induction part comprises an Arabinogalactan protein and/or a plant transcription factor associated with plant growth and development. The uptake enhancement part comprises a cell penetrating peptide sequence and a nuclear localization signal encoded by the peptide sequence SEQ ID NO 1.

13 Claims, 2 Drawing Sheets
Specification includes a Sequence Listing.

(56) References Cited

OTHER PUBLICATIONS

Pereira, Ana Marta, Luís Gustavo Pereira, and Sílvia Coimbra. "Arabinogalactan proteins: rising attention from plant biologists." Plant Reproduction 28 (2015): 1-15. (Year: 2015).*

Su, Shihao, and Tetsuya Higashiyama. "Arabinogalactan proteins and their sugar chains: functions in plant reproduction, research methods, and biosynthesis." Plant reproduction 31.1 (2018): 67-75. (Year: 2018).*

Egelkrout, Erin, Vidya Rajan, and John A. Howard. "Overproduction of recombinant proteins in plants." Plant science 184 (2012): 83-101. (Year: 2012).*

Hällbrink, Mattias, et al. "Prediction of cell-penetrating peptides." International Journal of Peptide Research and Therapeutics 11 (2005): 249-259. (Year: 2005).*

Chang, Shenghe, et al. "A method to improve the embryogenesis rate of banana somatic cell embryogenesis." American Journal of Plant Sciences 9.03 (2018): 531 (Year: 2018).*

Chang et al., "A Method to Improve the Embryogenesis Rate of Banana Somatic Cell Embryogenesis," American Journal of Plant Sciences, vol. 9, No. 3, Feb. 27, 2018, pp. 531-541.

Duchow et al., "Arabinogalactan-Proteins Stimulate Somatic Embryogenesis and Plant Propagation of Pelargonium Sidoides," Carbohydrate Polymers, vol. 152, Jul. 5, 2016, pp. 149-155.

Florez et al., "Enhanced Somatic Embryogenesis in Theobroma cacao using the Homologous Baby Boom Transcription Factor," BMC Plant Biology, vol. 15, No. 1, May 16, 2015, 13 Pages.

Kubota, "Concepts and Background of Photoautotrophic Micropropagation", Molecular Breeding of Woody Plants, Jan. 1, 2001, pp. 325-334.

Mizuno et al., "Cellular Internalization of Arginine-Rich Peptides into Tobacco Suspension Cells: A Structure-Activity Relationship Study," Journal of Peptide Science, vol. 15, Nov. 7, 2008, pp. 259-263.

Shu et al., "Tobacco Arabinogalactan Protein NtEPc can Promote Banana (Musa AAA) Somatic Embryogenesis," Applied Biochemistry and Biotechnology, vol. 174, No. 8, Sep. 18, 2014, pp. 2818-2826.

Extended European Search Report from corresponding European Application No. 19162059.0, May 28, 2019.

International Search Report and Written Opinion from PCT Application No. PCT/EP2020/056457, May 29, 2020.

* cited by examiner

TRANSCRIPTION FACTOR-MEDIATED PROMOTION OF DIRECT SOMATIC EMBRYOGENESIS

REFERENCE TO SEQUENCE LISTING SUBMITTED ON COMPUTER

The content of the ASCII text file of the sequence listing named "TR009WO-ST25.txt" which was filed in PCT/EP2020/056457 on Mar. 11, 2020, downloaded from the WIPO database, is 4 kb in size with a created date of Sep. 2, 2021, and electronically submitted via EFS-Web herewith the application, is incorporated herein by reference in its entirety.

TECHNICAL FIELD

The present invention relates to the field of micropropagation of plants, i.e. artificial plant reproduction by tissue culture techniques. More specifically, the invention relates to a method for micropropagation of Cannabis sativa L. plants, a recombinant protein, a cell culture medium comprising such recombinant protein and a method for producing the recombinant protein.

TECHNICAL BACKGROUND

Asexual reproduction of plants, e.g. by vegetative reproduction and/or tissue culture, can be useful in plant cultivation processes for agricultural and/or biochemical purposes. For example, plant to plant variation can be reduced by asexual reproduction, such that a chemical profile of a biomass product can be better controlled. Furthermore, single or few plants can be selected, based on preferential properties, for massive trait replication in a next generation of plants.

In vegetative propagation, cuttings may be taken from a mother plant and placed in a liquid rooting solution, under controlled humidity and temperature, to produce new roots, such that asexual copies of the mother plant are obtained. The growth of roots is driven by nutrition stores in the cutting, the humid environment and the substrate, and an imbalance in hormones signaling the cutting to create roots. However, it is a disadvantage of this approach that the quality of cutting clones is dependent on the condition of the mother plants. If the mother has mites, a virus, mold or nutrient deficiencies, the clone will have to combat such conditions while staying alive and forming new roots. Therefore, it is generally quite easy to carry plant diseases into the next generation. There is also an increased risk of mutations that may occur over time. Furthermore, since the mother plants are not immortal and need ongoing care, the rate at which clones can be harvested is limited.

As known in the art, micropropagation, or tissue culture, enables the rapid production of a large number of progeny plants from stock material. This technique is also useful for reproducing a particular genetic strain of interest, e.g. a novel genetically engineered or bred strain. Preferred strains can be kept indefinitely without the need of dedicated mother plants or propagation of new samples taken from production plants. Instead, tissues from mother plants can be kept and stored cryogenically, and reused when needed. Thus, a genetic lineage can be maintained in a suspended animation for prolonged periods of time (also known as 'tissue banking') without taking up large amounts of space to keep it protected from pests and diseases. Furthermore, pathogen-free transplants can be produced. Pests and diseases can be eliminated while preparing the plant tissue for cloning, i.e. a new generation will be sterile and will start free of pests and diseases. This approach may also be particularly useful for reproducing a plant that does not produce seeds or is difficult to reproduce by natural vegetative reproduction.

Typically, a section of healthy plant tissue is excised from a plant under sterile conditions. Explant material is then isolated, washed, sterilized and placed in a growth medium, e.g. containing an energy source, such as sucrose, essential nutrients and one or more plant growth regulators, e.g. hormones. The growth medium may typically be a gel, to support the explant during growth. This phase of the process, advantageously, can be carried out in vitro. The explant is kept cool and progresses through stages of growth, using differing hormones. Once the plant is large enough, it is cut, or "multiplied," into hundreds of plants. Each of the new cuttings, or clones, undergoes the same washing and gel process until they eventually are exposed to a different hormone to encourage root growth. The plantlets are then sufficiently developed to be slowly introduced, or "hardened-off," to a production growth environment. Since the plantlets were developing under ideal conditions for rapid growth, which can cause these plantlets to be susceptible to disease and inefficient in resource utilization, some time for adjustment to more natural conditions may be required, as provided by the hardening transition phase. Ultimately, new production plants are obtained that have identical genetics, are free of pests and diseases and can be produced by the thousands with incredible accuracy.

Unfortunately, a tissue culture process may take months and may require a high level of logistical organization to know and track the varieties needed for cultivation. Tissue culture technology is capital-intensive, e.g. expensive compared to conventional methods such as vegetative propagation, and requires specialized skills. In some cases, the cost of production can be so high that the unit cost per plant becomes unacceptably high. The economic viability and practical utility of this technique has always been doubted, for example in the forestry sector. Recent advances in tissue culture techniques and protocol have partially addressed the cost factor without compromising the quality of plants produced. Major contributing factors to the cost of a tissue culture plant are energy (electricity), labor and chemicals. In industrialized countries, labor is the main factor to be considered while reducing the cost of production. A commercial production unit, therefore, requires a constant monitoring of the input costs in terms of capital, chemicals, energy, labor and research and development work to develop better options to reduce cost of production.

Chemicals such as carbon sources, gelling agents, inorganic and organic supplements, and growth regulators in culture media also contribute to the cost of this technique. Sucrose is usually used as a source of carbon and agar as the gelling agent, which together constitute the most expensive components of the culture media.

Furthermore, some plant species are more recalcitrant to embryogenesis, i.e. to regeneration and/or transformation, which imposes limits on the embryos converting to plants, and thus on efficiency and profitability.

In view of these considerations, a need exists in the art for a viable, more efficient, more cost-effective alternative to current methods of traditional vegetative propagation and/or micropropagation.

As an example of methods known in the art, US 2016/286749 discloses the application of direct, as well as indirect, somatic embryogenesis in a process for propagating *Theobroma cacao* L.

Approaches to micropropagation, as known in the art, may use indirect somatic embryogenesis. This is a type of clonal propagation where cells derived from competent somatic source tissue are cultured to form an undifferentiated mass of cells, called a callus. Plant growth regulators in the tissue culture medium are manipulated to induce callus formation and subsequently changed to induce embryos to form from the callus. These embryos can subsequently be convered into plants. However, such tissue culture techniques can be cumbersome and there is significant variation between the protocols and conditions that are required to produce different plant types or species. For example, the ratio of different plant growth regulators required to induce callus or embryo formation may vary depending on the type of plant.

Processes known in the art that are based on direct somatic embryogenesis may involve the following sequence of steps: (i) induction of direct somatic embryogenesis, (ii) development of somatic embryos, (iii) multiplication of direct somatic embryos, (iv) germination of somatic embryos, and (v) conversion in plants of somatic embryos. However, direct somatic embryo production may not auger well for large-scale clonal propagation, since the number of direct embryos that are obtainable forms a limiting factor.

Whatever the regeneration pathway, plant tissue culture has emerged as an important biotechnology and commercially viable tool to generate high quality, disease free and high yielding planting material rapidly in the laboratory, irrespective of the season.

Embodiments of the present invention may be particularly suitable for the cultivation of *Cannabis*. *Cannabis* is a genus in the family Cannabaceae, also referred to as the hemp family, and the division Manoliophyta, i.e. the flowering plants. It is an annual, dioecious, flowering herb in which three species could be recognized: *Cannabis sativa*, *Cannabis indica*, and *Cannabis ruderalis*, even though *C. ruderalis* could also be included in *C. sativa*, such that *C. sativa* and *C. indica* could be considered as the two primary species. To some extent, the three species might even be treated as subspecies of a single species, *C. sativa*. Furthermore, Hemp and Marijuana are considered as species of *Cannabis* that are both members of the *Cannabis sativa* family. However, considerable confusion exists between the genus *Cannabis* and these species Hemp and Marijuana. Because these three terms are often used interchangeably, difficulties arise in understanding the usage and benefits of Hemp vs Marijuana and *Cannabis* in general. These fast-growing plants can be used as a source of phytochemicals and/or of fibers, e.g. cellulosic fibers and woody fibers. Its metabolites show potent bioactivities on human health and its outer and inner stem tissues can be used to make bioplastics and concrete-like material, respectively.

*Cannabis* has unique pharmacological properties due to the presence of cannabinoids, a group of more than 100 natural products that mainly accumulate in female flowers. 49-Tetrahydrocannabinol ("THC") is the principal psychoactive cannabinoid and the compound responsible for the analgesic, antiemetic and appetite-stimulating effects of *Cannabis*. Cannabinoid content and composition is highly variable among *Cannabis* plants. Selective breeding of *Cannabis* and improved cultivation practices have led to increased potency in the past decades. This breeding effort has produced hundreds of strains that differ in cannabinoid composition, as well as appearance and growth characteristics but can all be termed as "Marijuana". Hemp, on the other hand, often refers only to varieties of *Cannabis* that are cultivated for non-drug use. *Cannabis* has long been used for industrial hemp fibre, hemp seeds and their oils, hemp leaves for use as vegetables and as juice, and for medicinal purposes.

Recently, the increased medical and recreational legal use of *Cannabis* has led to a demand for improved cultivation and breeding practices thereby improving the quality and quantity of *Cannabis* available on the marketplace. The widespread medical use and the increasingly popular recreational use have caused supply shortages of this therapeutically and economically valuable crop.

*Cannabis* is a highly heterozygous species. Being a dioceous (male and female flowers appear on two different plants) and wind pollinated species, it is difficult to maintain the chemical profile of biomass product, if grown from seed. Plant to plant variation is continuously observed even though plants are grown from seeds obtained from a single female plant. Therefore, to maintain consistency in the end product, elite female plants are screened and multiplied using vegetative propagation and/or tissue culture.

Traditionally, most *Cannabis* growers use vegetative cloning. The cuttings from a mother plant are placed in a liquid rooting solution to produce new roots. They tend to be 7.5 to 15 cm tall with some foliage atop a stripped-down stem, somewhat resembling a small palm tree. On average, one has transplantable roots in healthy clones by day seven, although the unhealthy clones can take more than three times as long, especially if 're-vegging' a flowered branch. (Re-vegging can happen when the genetic lineage has accidentally flowered before a new generation is started) However, commercial *Cannabis* growers would benefit from the ability to produce high volumes of clones and keep preferred strains indefinitely without the need of dedicated mother plants, as would be offered by tissue culture techniques. Unfortunately, the cost of state-of-the-art tissue culture techniques is generally too high, for the reasons discussed hereinabove, and *Cannabis sativa* is a notorious recalcitrant plant to embryogenesis, which increases expenditures even more.

Approaches to micropropagation of *Cannabis sativa* L. and its related species, as known in the art, may use the technique of indirect somatic embryogenesis, in which undifferentiated calluses are obtained as a source of primary embryos. For example, propagation by indirect somatic embryogenesis of tissue explants in solid or (semi) liquid media, as known in the art, may comprise:

(i) primary embryogenesis in the dark in a solid culture medium for 5 to 15 weeks for causing induction and expression to produce primary embryos, (ii) secondary embryogenesis in which (A) the primary embryos are treated in the dark in solid or liquid media culture medium for 10 to 25 weeks to produce and multiply embryogenesis callus followed by (B) treatment of the embryogenesis callus in the dark in a suitable liquid culture medium for 1 to 6 weeks for causing expression of the embryogenesis callus to produce further new secondary embryos, (iii) pre-germination of the secondary embryos in a Petri dish on a solid medium, or in a bioreactor in a liquid medium for 3 to 12 weeks, into pre-germinated secondary embryos at the cotyledonary stage, (iv) ex-vitro germination of the pre-germinated secondary embryos at the cotyledonary stage by sowing directly on a culture substrate in the greenhouse to produce the plantlets, and (v) development of the plantlets.

However, such approach requires a long period to obtain somatic embryos and regenerated plants, and can result in a high amount of abnormal embryos. Furthermore, because of the reliance on formation of callus tissue, there is a higher probability of somaclonal variation among the regenerated plants. Considering the lengthy process and substantial amount of chemicals needed in the process, this technology still remains costly.

Duchow et al, in "Arabinogalactan-proteins stimulate somatic embryogenesis and plant propagation of *Pelagonium sidoides*," Carbohydrate Polymers, vol. 152, pp. 149-155, disclosed a stimulating effect of Arabinogalactan proteins on somatic embryogenesis and plant regeneration in *Pelagonium sidoides*.

Mizuno et al, in "Cellular internalization of arginine-rich peptides into tobacco suspension cells: a structure-activity relationship study," Journal of Peptide Science, vol. 15 (4), pp. 259-263, disclosed the potential use of arginine-rich peptides as intracellular delivery vectors in plants.

Chang et al, in "A method to improve the embryogenesis rate of banana somatic cell embryogenesis," American Journal of Plant Sciences, vol. 9 (3), pp. 531-541, disclosed a recombinant protein, Arg9-NLS-WIND1, that can be added to an embryonic callus inducing medium to improve the embryogenesis rate of banana somatic cell embryogenesis.

Shu et al, in "Tobacco arabinogalactan protein NtEPc can promote banana (Musa AAA) somatic embryogenesis," Applied Biochemistry and Biotechnology; Part A: Enzyme Engineering and Biotechnology, vol. 174 (8), pp. 2818-2826, disclosed a promoting effect of a tobacco Arabinogalactan protein on somatic embryogenesis of banana.

Florez et al, in "Enhanced somatic embryogenesis in *Theobroma cacao* using the homologous BABY BOOM transcription factor," BMC Plant Biology, vol. 15 (1), p. 121, disclosed the use of the transcription factor Baby Boom to promote the transition of somatic cacao cells from the vegetative to embryonic state.

Kubota et al, in "Concepts and background of photoautotrophic micropropagation," Progress in Biotechnology, Elsevier Science, vol. 18, pp. 325-334, discussed advantages of photoautotropic micropropagation.

SUMMARY

It is an object of embodiments of the present invention to provide viable, efficient, reproducible, and/or cost-effective means and methods for, or relating to, the micropropagation of *Cannabis sativa* L. plants.

It is an advantage of embodiments of the present invention that means and methods in accordance with embodiments of the present invention may be particularly suitable for the cultivation of *Cannabis*, e.g. of *Cannabis sativa* L. plants. For example, a reproducible tissue culture process can be provided for the regeneration of a large number of *Cannabis sativa* L. plants from their explants, which may obviate the drawbacks of processes known in the art, e.g. as broadly outlined hereinabove.

Embodiments of the present invention may be based, e.g. or may be based at least in part, on the surprising discovery that it is possible to induce direct somatic embryogenesis, e.g. in liquid or solid media, by exposing the explant material to one or more recombinant plant transcription factors and/or Arabinogalactan proteins. These transcription factors and/or Arabinogalactan proteins may be associated with plant growth and development, including embryogenesis and cell proliferation.

It is an advantage of embodiments of the present invention that a method of micropropagation in accordance with embodiments can be more efficient and/or more cost-effective than a traditional method of vegetative propagation and/or a method of micropropagation as known in the art.

It is an advantage of embodiments of the present invention that a large number of viable plants of interest, e.g. *Cannabis* plants, can be produced in vitro.

It is an advantage of embodiments of the present invention that large scale micropropagation can be useful for selection of mutants of interest, production of plants with altered levels of endogenous secondary metabolites and/or genetic engineering.

It is an advantage of embodiments of the present invention that a method in accordance with embodiments may be particularly suitable and advantageous for the production of *Cannabis* plants.

It is an advantage of embodiments of the present invention that a high conversion rate of embryos to plantlets can be achieved. It is an advantage of embodiments of the present invention that somatic embryos per batch can be improved or increased. It is an advantage of embodiments of the present invention that embryogenesis and conversion of embryos to viable plantlets can be significantly increased, e.g. compared to at least one prior art method, by adding specific recombinant transcription factors and/or Arabinogalactan proteins to plant cell culture media.

It is an advantage of embodiments of the present invention that a cell penetrating peptide sequence, e.g. a Poly-Arg Transduction Domain, and/or a nuclear localization signal or sequence (NLS) can be fused to one of the recombinant transcription factors or the Arabinogalactan protein such that the cell penetrating peptide sequence, e.g. the Poly-Arg Transduction Domain, can bind with cell membranes and be transferred quickly into the cell and/or such that the NLS tags a protein for import into the cell nucleus by nuclear transport.

It is an advantage of embodiments of the present invention that a cell penetrating peptide sequence, e.g. a Poly-Arg Transduction Domain, and/or an NLS fused to the recombinant transcription factor or Arabinogalactan protein can be guided into the nucleus of plant cells to efficiently induce embryogenesis response of plant somatic cells.

It is an advantage of embodiments of the present invention that the recombinant fusion construct can be easily expressed and purified using transient expression in *Nicotiana benthamiana* plants as a high throughput platform for large scale and/or low cost production. However, other expression host organisms, such as bacteria, yeast, insect, mammalian, or other plant expression systems, are also within the scope of the present invention.

Other objects, advantages, and novel features will be readily apparent to those skilled in the art from the following detailed description of the invention.

In a first aspect, the present invention relates to a recombinant protein for use in a liquid culture medium for photoautotrophic micropropagation of *Cannabis sativa* L. The recombinant protein comprises a fusion of a growth induction part and a uptake enhancement part, wherein said growth induction part comprises an Arabinogalactan protein and/or a plant transcription factor associated with plant growth and development, wherein said uptake enhancement part comprises a cell penetrating peptide sequence and a nuclear localization signal. The nuclear localization signal is encoded by the sequence SEQ ID NO: 1.

A recombinant protein in accordance with embodiments of the present invention may be encoded by the coding sequence SEQ ID NO: 2, e.g. which may be codon optimized to *Nicotiana* species.

In a recombinant protein in accordance with embodiments of the first aspect of the present invention, the uptake enhancement part may comprise said cell penetrating peptide sequence, said cell penetrating peptide sequence comprising a sequence of 7 to 13 arginines, preferably 9 arginines, forming a poly-arginine transduction domain. (see e.g. SEQ ID NO 3)

In a recombinant protein in accordance with embodiments of the first aspect of the present invention, the growth induction part may comprise said plant transcription factor, said plant transcription factor comprising one or more of: Baby Boom, BBM (e.g. UnitprotKB/Swiss-Prot, accession ID: Q6PQQ4, entry version 114, sequence version 2, sequence date 2005 Aug. 30, entry date 2020 Feb. 26), Leafy Cotyledon, LEC, e.g. B3 domain-containing transcription factor LEC2 (e.g. UniprotKB/Swiss-Prot, accession ID: Q1PFR7, entry version 89, sequence version 1; sequence date 2006 May 16, entry date 2020 Feb. 26), Wuschel, WUS (e.g. UniprotKB/Swiss-Prot, accession ID: Q9SB92, entry version 139, sequence version 2, sequence date 2005 Mar. 15, entry date 2020 Feb. 26), RWP-RK Domain-Containing 4, RKD4 (e.g. UniProtKB/Swiss-Prot, accession ID: Q9LVU8, entry version 86, sequence version 1, sequence date 2000 Oct. 1, entry date 2020 Feb. 26), Wound Induced Dedifferentiation 1, WIND1 (e.g. UniProtKB/Swiss-Prot, accession ID: A0A178WKP5, entry version 21, sequence version 1, sequence date 2016 Sep. 7, entry date 2019 Dec. 11), and Plethora2, PLT2 (e.g. UniProtKB/Swiss-Prot, accession ID: Q5YGP7, entry version 110, sequence version 1, sequence date 2004 Nov. 23, entry date 2020 Feb. 26).

In a recombinant protein in accordance with embodiments of the first aspect of the present invention, said plant transcription factor may comprise AP2-like ethylene-responsive transcription factor BBM from *Arabidopsis thaliana*, or an analog to said AP2-like ethylene-responsive transcription factor BBM from *Arabidopsis thaliana*, wherein said analog is codon-optimized for a host species.

In a recombinant protein in accordance with embodiments of the first aspect of the present invention, said host species may be *Nicotiana benthamiana*.

In a second aspect, the present invention relates to a plant cell culture medium comprising a recombinant protein in accordance with embodiments of the first aspect of the present invention.

A plant cell culture medium in accordance with embodiments of the second aspect of the present invention may comprise the recombinant protein in a concentration in the range of 0.05 mg/L to 5 mg/L.

A plant cell culture medium in accordance with embodiments of the second aspect of the present invention may comprise salts and/or vitamins.

A plant cell culture medium in accordance with embodiments of the second aspect of the present invention may comprise one or more of the following: 6-benzylaminpurine, Ethephon, Kinetin, Putrescine, Spermidine, Hydrogen Peroxide, 6-(Y,Y-dimethylallylamino) purine, Gibberellic Acid or Gibberellin, and Naphthaleneacetic Acid.

A plant cell culture medium in accordance with embodiments of the second aspect of the present invention may be a liquid culture medium for photo-autotrophic micropropagation.

In a third aspect, the present invention relates to a method for micropropagation of *Cannabis sativa* L. The method comprises obtaining explant material from a *Cannabis sativa* L. plant, and providing primary and/or secondary embryos by inducing embryogenesis in the explant material in a plant cell culture medium in accordance with embodiments of the second aspect of the present invention.

In a method in accordance with embodiments of the third aspect of the present invention, providing primary and/or secondary embryos may comprise a photoautotrophic method in which the explant material is exposed to light for stimulating direct somatic embryogenesis.

In a method in accordance with embodiments of the third aspect of the present invention, said exposure to light comprises the exposure to light from a photo-synthetically active radiation (PAR) source, in the wavelength range of 400 nm to 700 nm, and at a photosynthetic photon flux between 100 and 200 µmol m$^{-2}$ s$^{-1}$.

The independent and dependent claims describe specific and preferred features of the invention. Features of the dependent claims can be combined with features of the independent claims and with features of other dependent claims as deemed appropriate, and not necessarily only as explicitly stated in the claims.

SHORT DESCRIPTION OF THE DRAWINGS

FIG. 1 shows a longitudinal section of globular embryo development on the surface of the explant (bar=50 mm).

FIG. 2 shows a longitudinal section of early heart-shaped embryo (bar=50 mm).

FIG. 3 shows a longitudinal section of late heart-shaped embryo (bar=50 mm).

FIG. 4 shows a longitudinal section of somatic embryo (cotyledonary stage) showing two distinct cotyledons with root meristem (bar=50 µm).

Figure 1:
FIG. 1 to FIG. 4 illustrate the histology of somatic embryogenesis of *Cannabis sativa* L., in an example relating to a process in accordance with embodiments of the present invention.

The drawings are schematic and not limiting. Elements in the drawings are not necessarily represented on scale. The present invention is not necessarily limited to the specific embodiments of the present invention as shown in the drawings.

DETAILED DESCRIPTION

Notwithstanding the exemplary embodiments described hereinbelow, is the present invention only limited by the attached claims. The attached claims are hereby explicitly incorporated in this detailed description, in which each claim, and each combination of claims as allowed for by the dependency structure defined by the claims, forms a separate embodiment of the present invention.

The word "comprise," as used in the claims, is not limited to the features, elements or steps as described thereafter, and does not exclude additional features, elements or steps. This therefore specifies the presence of the mentioned features without excluding a further presence or addition of one or more features.

In this detailed description, various specific details are presented. Embodiments of the present invention can be carried out without these specific details. Furthermore, well-known features, elements and/or steps are not necessarily described in detail for the sake of clarity and conciseness of the present disclosure.

The embodiments of the present invention are specifically described below with reference to the embodiments, so as to facilitate the understanding of the present invention by those skilled in the art. It should be noted that the embodiments are only used for further explanation of the present invention. The embodiments cannot be understood to limit the protection scope of the present invention. A person skilled in the art will recognize that the protection scope of the present invention can be better understood by those skilled in the art. The non-essential improvement and adjustment made by the method disclosed by the invention should still be within the protection scope of the invention. Meanwhile, raw materials being used are not always described in detail. The raw materials may be commercially available products. The process steps or preparation methods that are not always described in detail are process steps or preparation methods which are known by those skilled in the art. *Cannabis sativa* L. (industrial fiber hemp) is used throughout the present disclosure as an example.

In a first aspect, the present invention relates to a recombinant protein comprising a fusion of a growth induction part and a uptake enhancement part. The growth induction part comprises an Arabinogalactan protein and/or at least one plant transcription factor associated with plant growth and development, e.g. associated with embryogenesis and/or cell proliferation. The uptake enhancement part comprises a cell penetrating peptide sequence and a nuclear localization signal or sequence.

The recombinant protein may be a recombinant protein suitable for, e.g. designed for, inducing and/or improving embryogenesis when explant tissue material, or cultured cell plant material, is exposed to the recombinant protein.

In a recombinant protein in accordance with embodiments of the present invention, the cell penetrating peptide sequence may comprise a sequence of arginines forming a poly-arginine (Poly-Arg) transduction domain. The poly-arginine transduction domain may consist of a sequence that consists of 9 arginine residues (RRRRRRRRR), corresponding to SEQ ID NO: 3. The cell penetrating peptide sequence may be adapted for efficiently translocating the protein across cells, e.g. through cell membranes.

In a recombinant protein in accordance with embodiments of the present invention, the nuclear localization sequence may be adapted for tagging the recombinant protein, e.g. entirely or at least the growth induction part thereof, for import into the cell nucleus by nuclear transport. Typically, an NLS consists of one or more short sequences of positively charged lysines or arginines exposed on the protein surface. In the present disclosure, the NLS is encoded by, e.g. corresponds to, the peptide sequence SEQ ID NO: 1.

In a recombinant protein in accordance with embodiments of the present invention, the growth induction part may comprise the at least one plant transcription factor, in which the at least one plant transcription factor comprises one or more of: Baby Boom (BBM), Leafy Cotyledon (LEC), Wuschel (WUS), RWP-RK Domain-Containing 4 (RKD4), Wound Induced Dedifferentiation 1 (WIND1), and Plethora2 (PLT2).

For example, the Baby Boom Transcription Factor (AP2-like ethylene-responsive transcription factor BBM) gene, may be involved in the acquisition of embryogenic competence by somatic cells. BBM is a transcription factor of the AP2/ERF family that is expressed in seed and root meristem. It was originally isolated as a marker for embryogenic cells in tissue culture, which activates a complex network of developmental pathways associated with cell proliferation and growth. BBM expression was observed in microspore-derived embryos of *Brassica napus* and basal region of *Arabidopsis thaliana* zygotic embryos. It was also identified in root meristems and lateral roots of *Arabidopsis* seedlings and, as an auxin-inducible gene, in *Medicago truncatula* roots. The BBM gene is expressed early during microspore embryogenesis of *Brassica napus*, and it is postulated that the BBM gene is involved in the conversion from vegetative to embryogenic state of development. Ectopic expression of BBM in *Arabidopsis thaliana* and *Brassica napus* induces spontaneous somatic embryos and cotyledon-like structures formation from the vegetative tissues of young seedlings. Similar effects can be induced by constitutive expression of GmBBM in *Arabidopsis*. In tobacco, heterologous BBM expression led to spontaneous formation of shoots and callus indicating its role in promoting cell proliferation and morphogenesis.

If BBM is over-expressed in plant cell material of interest, such as *Cannabis sativa* L. plant cell material, embryogenesis may be advantageously induced. However, to express a foreign transcription factor, e.g. BBM, into the plant material of interest, the transcription factor needs to be transferred effectively into the cell and into the nucleus. It is an advantage of a recombinant protein in accordance with embodiments of the present invention that such efficient and effective transfer can be achieved.

For example, the plant transcription factor may comprise AP2-like ethylene-responsive transcription factor BBM from *Arabidopsis thaliana* (BBM_ARATH-UniProt: Q6PQQ4, version 110, 16-01-2019), or an analog to said AP2-like ethylene-responsive transcription factor BBM from *Arabidopsis thaliana*, wherein said analog is codon optimized for a host species suitable for expression in a production environment, such as *Nicotiana benthamiana*.

In a preferred embodiment, the recombinant protein comprises, or consists of, a fusion of the 9 arginine residues (Arg9), the nuclear localization signal or sequence is encoded by the peptide sequence SEQ ID NO: 1 (NLS), and the AP2-like ethylene-responsive transcription factor BBM from *Arabidopsis thaliana* or its analog codon optimized for *Nicotiana benthamiana*. This recombinant protein may be referred to as "Arg9-NLS-BBM" hereinbelow.

Transactivator of transcription (TAT) protein transcription domain (PTD) is a special 10-20 amino acid sequence derived from HIV TAT protein. Once added into a culturing media, TAT-fusion protein can rapidly enter the cells. Within cells, the TAT-fusion protein is either degraded or refolded by the cellular machinery into functional protein. Most of the TAT PTD contains Arg and Lys aminoacids, which have strong positive charge. Therefore, it was postulated that these amino acid sequences could bind with the cell membrane and be transferred into the cell quickly. The Poly-Arg transduction domain is an artificial sequence according to the sequences of transduction domains found. Its transduction efficiency is higher than TAT PTD derived from HIV. Experiments showed that it can be used to lead the foreign protein to transfer the cell membrane.

Therefore, by linking the growth induction part, e.g. comprising the BBM transcription factor, with a poly-Arg transduction domain as uptake enhancement part, a good transfer into the cell can be obtained. Furthermore, by also linking a nuclear localization signal or sequence (NLS) to this construct, the recombinant protein can be tagged for import into the cell nucleus by nuclear transport. The mechanism of 'nuclear import', is quite straightforward: proteins gain entry into the nucleus through the nuclear envelope. The nuclear envelope consists of concentric membranes, the outer and the inner membrane. The inner and outer membranes connect at multiple sites, forming channels between the cytoplasm and the nucleoplasm. These channels are occupied by nuclear pore complexes (NPCs), complex multiprotein structures that mediate the transport across the nuclear membrane.

A protein translated with a NLS will bind strongly to importin (aka karyopherin), and, together, the complex will move through the nuclear pore. At this point, Ran-GTP will bind to the importin-protein complex, and its binding will cause the importin to lose affinity for the protein. The protein is released, and now the Ran-GTP/importin complex will move back out of the nucleus through the nuclear pore. A GTPase-activating protein (GAP) in the cytoplasm hydrolyzes the Ran-GTP to GDP, and this causes a conformational change in Ran, ultimately reducing its affinity for importin. Importin is released and Ran-GDP is recycled back to the nucleus where a Guanine Nucleotide Exchange Factor (GEF) exchanges its GDP back for GTP.

In a second aspect, the present invention relates to a plant cell culture medium comprising a recombinant protein in accordance with embodiments of the first aspect of the present invention. The plant cell culture medium may be a suitable cell culture medium for use in direct primary and/or secondary somatic embryogenesis, e.g. for substantially increasing an embryogenesis rate of somatic cells, e.g. of *Cannabis sativa* L. somatic cells, when exposed to the cell culture medium. The plant cell culture medium may be a suitable autotrophic cell culture medium for use in the maturation and/or pre-germination of direct somatic embryos, e.g. of *Cannabis sativa* L. somatic cells, when exposed to the cell culture medium. The plant cell culture medium may be a suitable autotrophic cell culture medium for use in the germination of direct somatic embryos, e.g. of *Cannabis sativa* L. somatic cells, when exposed to the cell culture medium. The plant cell culture medium may be a suitable autotrophic cell culture medium for use in the shoot elongation and rooting of direct somatic embryos, e.g. of *Cannabis sativa* L. somatic cells, when exposed to the cell culture medium.

The recombinant protein in accordance with embodiments of the first aspect of the present invention, e.g. such as the Arg9-NLS-BBM recombinant protein, may be provided in an amount, e.g. a concentration, in the range of 0.05 mg/L to 5 mg/L, preferably in the range of 0.5 mg/L to 3 mg/L, and more preferred, about 2 mg/L.

The plant cell culture medium may comprise a viral vector.

The plant cell culture medium may comprise components necessary for the induction and development of primary embryos as understood in the art. For example, the medium may comprise a source of energy (i.e. a usable source of energy for the plant), such as sucrose. The medium may comprise nutrients. However, in other embodiments in accordance with the present invention, the medium does not comprise a source of energy, e.g. does not comprise a substantial amount of any source of energy. The medium may comprise macro and/or micro salts, e.g. in solution. The medium may comprise vitamins.

The plant cell culture medium may be suitable for use as a medium in photoautotrophic micropropagation. Where in the present application reference is made to photoautotrophic media and/or processes, it is understood that this refers to a medium and/or process for micropropagation in which no substantial amount of sugar is included in the medium. Even though photoautotrophy could be defined even more narrowly as a nutritional type where living organisms grow without any additional xenogenous organic components as nutrients, e.g. such that the photoautotrophic medium excludes all organic components, the use of the term photoautotrophy is intended as less restrictive in the present application, i.e. photoautotrophy refers to the plant nutritional type where only endogenous carbohydrate is used as the principal energy source, such that, for practical purposes, photoautotrophic micropropagation refers to micropropagation with (substantially) no sugar provided by the medium to the plant for its energy requirements. However, sugar and/or other carbohydrates may be significant components of agar and other gelling agents, in which case such sugar and/or other carbohydrates are not necessarily considered as a substantial exogenous carbohydrate source for the practical definition of photoautotrophic micropropagation.

The medium may also comprise one or more plant growth regulators, and/or one or more growth hormones. The medium may comprise one or more of the following: 6-benzylaminpurine (BAP), Ethephon, Kinetin, Putrescine, Spermidine, Hydrogen Peroxide, 6-(Y,Y-dimethylallylamino) purine (2iP), and Gibberellic Acid/Gibberellin.

The medium may comprise a synthetic auxin. The medium may comprise the phytohormone 2,4-Dichlorophenoxyacetic acid (2,4D). However, in a preferred embodiment, the medium does not comprise the phytohormone 2,4D, since this is known to produce somaclonal variation and a large amount of embryos that cannot be converted into plants. The synthetic auxin may comprise Naphthaleneacetic Acid (NAA), e.g. 1-Naphthaleneacetic Acid. This synthetic auxin may be provided in amounts capable of supporting direct somatic embryogenesis, for example, 0.01 mg/L, 0.05 mg/L, 0.10 mg/L, 0.20 mg/L, 0.30 mg/L, 0.50 mg/L, 0.75 mg/L, 1.0 mg/L, 1.25 mg/L, 1.5 mg/L, 1.75 mg/L, 2.0 mg/L, 2.25 mg/L, 2.5 mg/L, 2.75 mg/L, or 3.0 mg/L., more preferably 1.0 mg/L, or a concentration in any range formed by two endpoints selected from this exemplary list hereinabove.

The plant cell culture medium may be a photomixotrophic and/or photoheterotrophic culture medium. However, in a preferred embodiment, the plant cell culture medium may be a photoautotrophic culture medium.

A particular example of the composition of a plant cell culture medium in accordance with embodiments of the present invention, comprising $NaNO_3$, NAA and the Arg9-NLS-BBM recombinant protein, is detailed in the table TABLE A hereinbelow. This composition may be particularly suitable as medium for inducing embryogenesis.

TABLE A

| Micro-elements | Concentration [mg/l] |
| --- | --- |
| $CoCl_2 \cdot 6H_2O$ | 0.025 |
| $CuSO_4 \cdot 5H_2O$ | 0.025 |
| FeNaEDTA | 36.70 |
| $H_3BO_3$ | 6.20 |
| KI | 0.83 |
| $MnSO_4 \cdot H_2O$ | 16.90 |
| $Na_2MoO_4 \cdot 2H_2O$ | 0.25 |
| $ZnSO_4 \cdot 7H_2O$ | 8.60 |

| Macro-elements | Concentration [mg/L] |
| --- | --- |
| $CaCl_2$ | 332.02 |
| $KH_2PO_4$ | 170.00 |
| $KNO_3$ | 1900.00 |
| $MgSO_4$ | 180.54 |
| $NaNO_3$ | 1751.00 |

TABLE A-continued

| Additions | |
|---|---|
| C$_6$H$_8$O$_7$ | 10.0 |
| C$_{12}$H$_{10}$O$_2$ (NAA) | 1.0 |
| Arg9-NLS-BBM | 2.0 |

A particular example of the composition of a plant cell culture medium in accordance with embodiments of the present invention, comprising NaNO$_3$, BAP, Amino Acid Stock 100× and the Arg9-NLS-BBM recombinant protein, is detailed in the table TABLE B hereinbelow. This composition may be particularly suitable as medium for embryo maturation.

TABLE B

| Micro-elements | Concentration [mg/l] |
|---|---|
| CoCl$_2$•6H$_2$O | 0.025 |
| CuSO$_4$•5H$_2$O | 0.025 |
| FeNaEDTA | 36.70 |
| H$_3$BO$_3$ | 6.20 |
| KI | 0.83 |
| MnSO$_4$•H$_2$O | 16.90 |
| Na$_2$MoO$_4$•2H$_2$O | 0.25 |
| ZnSO$_4$•7H$_2$O | 8.60 |

| | Concentration [mg/L] |
|---|---|
| Macro-elements | |
| CaCl$_2$ | 332.02 |
| KH$_2$PO$_4$ | 170.00 |
| KNO$_3$ | 1900.00 |
| MgSO$_4$ | 180.54 |
| NaNO$_3$ | 1751.00 |
| Additions | |
| C$_6$H$_8$O$_7$ | 10.0 |
| C$_{12}$H$_{11}$N$_5$ (BAP) | 1.0 |
| Amino Acid Stock 1000X | 2.0 |
| Arg9-NLS-BBM | 2.0 |

The plant cell culture medium may also comprise an elicitor, e.g. in a concentration of from about 0.01 µM to about 1 M, preferably in a concentration from about 1 µM to about 500 mM, more preferably in a concentration of between about 10 UM to about 200 mM and most preferably in a concentration of between about 50 µM and about 50 mM.

The elicitor agent or agents may be selected from one or more of biotic elicitors, microbial fractions or products derived from biotic elicitors, and abiotic elicitors. Examples of suitable elicitor agents include biotic elicitors such as: *Botrytis cinerea Phytophthora megasperma, Pinellas stripticum, Oligosporas* sp., *Pythium mamiallatum, Pythium sylvaticum, Verticillium dahliac, Verticillium* sp., *Penicillium minioluteum, Phytophthora lateralis, Cytospora cincta, Cytospora leucostoma, Alternaria brassicicola, Alternaria solani, Alternaria cucumerina, Botrytis squamosa, Cochliobolus heterostrophus, Colletotrichum trifolii, Colletotrichum orbiculum, Colletotrichum graminicola, Colletotrichum glocosporioides, Cylindrocladium floridanum, Fusarium crookwellense, Fusarium heterosporium, Fusarium oxysporam* f. sp. *conglutinans, Fusarium oxysporam* f. sp. *lycopersici, Fusarium oxysporam* f. sp. *pisi, Gibberella zeac, Gacumaimomyces graminis* var. *tritici, Geotrichum* sp., *Leptosphaeria torrae, Nectria haematococca* MPVI, *Mycosphaerella pinodes, Ophiostoma ulmi, Phoma lingam, Phoma pinodella, Phytophthora infestans, Pythium aristosporum, Pythium graminicola, Pythium ultimum, Rhizoctonia solani, Sclerotinia* sp., *S. nodoram* D-45, *Trametes versicolor, Ustilago maydis, Venturia inequalis*; microbial fractions or products derived from biotic clicitors such as: Chitosan, Lichenan, Glucomannan, Pleuran, Glucan, Carboxymethylglucan, Hydroxymethylglucan, Sulfoethylglucan, Mannan, Xylan, Mannobiose, Mannotriose, Mannopentaose, Mannotetraose, Cellulysin, Multifect XL, Multifect CL, Resinase, Pulpxyme, SP431, Pectinol, Rapidase, Klerzyme, Chitinase; or abiotic elicitors such as: Arachidonic acid, Elaidic acid, Cyclic AMP, Dibutyrl Cyclic AMP, Methyl Jasmone, Cis-Jasmone, Jasmonic acid,/3-glucan, Miconazol, Ferulic acid, AMO-1618, Triton X-100, Benzoic acid, Salicylic acid, Propyl gallate, Sesamol, Chlorocholine chloride, 3,4-dichlorophenoxy tricthyl-, (amine), Chloroethylphosphonic acid, Diethyldithiocarbamic acid, Nordihydroguairetic acid, Dithiothreitol, Sodium metabisulfite, Potassium metabisulfite, d-amino-DL-Phenylalanine, Vanadyl sulfate, Uniconazol, Paclobutrazol, Spermine, Spermidine, Putrescine, Cadavarine, Protamine Sulfate, SKF-7997, MER 29, Ancymidol, Triadimefon, Phosphon D, Thiourca, Dextran Sulfate, Hydroquinone, Chitosan glutamate, Fenpropemorph, Prochloraz, Naptifine, EDU, HTA, MPTA, Glutathione, EGTA, Gibberellins, Abscisic Acid, 1,3-Diphenyl urea, Diazolidenyl urea, Phloroglucinol, Sodium alginate, Carrageenan, Aluminium chloride, Ethylene, Acetylsalicylic acid, Sodium chloride, Acetic acid.

However, the medium may also be provided as a kit of parts, comprise a primary medium and the elicitor or elicitors as separate entities. In use, e.g. in a method in accordance with embodiments of the present invention, the elicitor(s) may be added to the culture (formed using the primary culture medium and cells of interest) at a time from the inoculation time to any time during the culture duration, preferably at a time from the early exponential growth phase to the stationary phase, depending on the natures of the metabolites and the cell line of the particular plant species.

Furthermore, a plurality of elicitors can be provided as separate entities in the kit of parts, such that a second or further addition of an elicitor(s) into the suspension culture can be performed in use, e.g. conducted between about six hours to about a month in duration after the previous elicitation, more preferably between about twelve hours to about two weeks in duration after the previous elicitation, and most preferably between about twelve hours to about seven days in duration after the previous elicitation.

The plant cell culture medium may comprise both Benzylaminopurine (BAP) and Meta-Topolin (MT), e.g. as a particularly advantageous combination for stimulating plant growth and development, shoot elongation and rooting of plantlets.

The plant cell culture medium may be in a liquid, a semiliquid, or a solid form. For example, the plant cell culture medium may comprise a porous supporting agent to form a solid medium, such as Florialite, a mixture of paper pulp and vermiculite (Nisshinbo Industries Inc., Tokyo). The plant cell culture medium may preferably be a liquid medium, e.g. which may result in a shorter overall process for obtaining plantlets when used. For example, when used in a method in accordance with embodiments of the present invention to produce *Cannabis sativa* L. plants, the production of a large number of embryos using solid media may take 13 to 16 months, while the production of a large number of embryos using primarily liquid media may take only 6 to 9 months, e.g. using a method in accordance with embodiments of the third aspect of the present invention.

In a third aspect, the present invention provides a method for micropropagation of plants. Embodiments of the present invention relate generally to a biotechnological approach to an efficient and/or cost-effective micropropagation method for propagating plants (e.g. in vitro), capable of increasing the rate of embryos to plantlets, e.g. suitable for propagating plants of a *Cannabis sativa* species.

The micropropagation method comprises obtaining explant material, e.g. a piece or pieces of tissue removed from a plant to be propagated. The micropropagation method may be particularly suitable for propagation of *Cannabis* plants, e.g. of *Cannabis sativa* L. plants. However, the micropropagation method may equally be applicable to, e.g. at least to, other plants within the family of Cannabaceae and other phytopharmaceutical plants selected from the group consisting of; *Achillea millefolium, Achyranthes bidentate, Aconitum napellus, Adonis aestivalis, Agastache Mexicana, Agrimonia cupatoria, Agathosma betulina, Allium* sp, *Anchusa officinalis, Anemopsis californica, Angelica dahurica, Angelica polymorpha sinensis (A. sinensis), Arnica Montana, Ammi visnaga, Arctostaphylos uva-ursi, Asclepias tuberosa, Astragalus membranaceus, Astragalus chinensis, Baphicacanthus cusia, Bixa Orellana, Bupleurum falcatum, Bragmansia (Datura)* spp., *Campanula rapunculus, Carum roxburgianum, Carum copticum, Cassia tora, Chamaelirium luteum, Chimaphila umbellate, Commiphora Africana, Conium maculatum, Crithium maritimum, Datura metel (Datura alba), Datura inoxia, Dracocephalum moldavica, Echinacea* sp., *Eclipta alba (E. prostrata), Ephedra nevadensis, Eriodictyon californicum, Eucommia ulmoides, Eupatorium perfoliatum, Filipendula vulgaris (F. hexapetala), Gaultheria procumbens, Geum urbanum, Houttuynia cordata, Hydrocotyle asiatica (Centella asiatica), Hypericum perforatum* cv. *Anthos, Inula helenium, Jatropha curcas, Leptospermum scoparium, Lespedeza capitate, Ligusticum porter, Ligustrum lucidum, Lithospermum officinale, Lycium barbarum, Mucuna pruriens, Mandragora officinarum, Origanum dictamnus, Parietaria judaica (P. officinalis), Phyllanthus emblica, Picrasma excelsa, Piniella ternate, Pogostemon patchouli, Polygonum multiflorum, Porophyllum raderale* ssp. *Macrocephalum, Prunella vulgaris, Pueraria lobata (P. thunbergiana), Rauvolfia serpentine, Rivea corymbose, Sanguinaria Canadensis, Satureja douglasii, Schizonepeta tenuifolia Scutellaria baicalensis, Solanum xanthocarpum (S. surattense), Sutherlandia frustescens, Tabebuia impetiginosa, Tanacetum parthenium, Tribulus terrestris, Trichosanthes kirilowii, Turnera diffusa, Voacanga africana*, and, *Withania somnifera*.

In a preferred embodiment, obtaining the explant material may comprise obtaining explant material from a *Cannabis sativa* L. plant. The explant material may be derived from leaves, fruit, shoots, buds, flowers, bark, roots, branches, stems, seeds, cones, needles or cambium tissue of the plant. In a particularly preferred embodiment of the invention the cells may be derived from hypocotyl meristematic end plant tissue.

The micropropagation method comprises providing primary and/or secondary embryos by inducing embryogenesis by placing the explant material and/or cell material derived therefrom in a plant cell culture medium in accordance with embodiments of the second aspect of the present invention. Preferably, the induced embryogenesis is a direct somatic embryogenesis process, in which embryos initiate directly from explants in the absence of callus formation. Embryos are thus formed by Pre-Embryonic Determined Cells (PDCs). Such cells are found mostly in embryonic tissues, certain tissues of young in vitro grown plants, hypocotyl, nucellus, embryo-sac, and the like. Thus, providing primary and/or secondary embryos may comprise a photoautotrophic method for (e.g. in vitro) multiplication of direct somatic embryos (DSEs) using direct somatic embryogenesis. Providing primary and/or secondary embryos may comprise exposure to light, e.g. substantially continuous exposure to light during the step of developing primary and/or secondary embryos. Th exposure to light may comprise exposure to photo-synthetically active radiation (PAR), e.g. from a PAR source. The PAR may comprise or consist of light having a wavelength or wavelengths in the range of 400 to 700 nm. The PAR may be provided in a photosynthetic photon flux in the range of 100 to 200 $\mu mol\ m^{-2}\ s^{-1}$, preferably during both development of primary embryos as during development of secondary embryos. The light is preferably provided in a 24-hour continuous light cycle. Such light conditions may be particularly suitable for propagation of *Cannabis sativa* L. plants.

However, embodiments of the present invention are not necessarily limited to direct somatic embryogenesis, e.g. may relate to indirect somatic embryogenesis, single cell culture, non-zygotic embryogenesis, shoot & root culture, meristem culture, anther culture, somatic hybridization, embryo culture, ovule culture, ovary culture, hairy root culture, and the like.

It is an advantage of somatic embryogenesis that it constitutes a highly efficient method for propagation of plants (such as *Cannabis sativa* L.). Somatic embryogenesis can provide large quantities of high-quality planting material. Furthermore, a good genetic quality and plant health can be achieved. Somatic embryogenesis is a type of clonal propagation where competent cells in the somatic tissue can develop into embryos and subsequently convert into plants. A somatic embryogenesis process can be used for the clonal propagation of genetically uniform plant material, for eliminating viruses, for providing source tissue for genetic transformation, for generating whole plants from single cells and for developing synthetic seed technology.

For example, in a preferred embodiment, the plant cell culture medium comprises the recombinant protein comprising the plant transcription factor BBM. For example, by over-expressing BBM in *Cannabis sativa* L., embryogenesis can be induced easily. Preferably, Arg9 and NLS components of the recombinant protein may efficiently and effectively transfer BBM into the *Cannabis sativa* L. nucleus.

Providing primary and/or secondary embryos may comprise providing primary embryos by direct somatic embryogenesis, e.g. using a photoautotrophic method. In such step, the explant material may be placed in an induction medium that comprises or consists of the plant cell culture medium in accordance with embodiments of the second aspect of the present invention and exposed to light, e.g. for a period sufficient to obtain primary embryos. The primary embryos may optionally be transferred from the induction medium to a development medium and cultured with exposure to light for a period sufficient to further expand the primary embryos.

Providing primary and/or secondary embryos may comprise providing secondary embryos by direct somatic embryogenesis. Providing the secondary embryos may comprise removing tissue from the primary embryos, such as epicotyls of primary embryos. The tissue removed from the primary embryos may, optionally, be cut into pieces. Although the tissue can be obtained from the torpedo embryos attained in the photoautotrophic step in which explant material is developed in the induction medium, in accordance with other embodiments of the present invention, the tissue may be obtained from epicotyl material derived from primary embryos after the optional step of further expanding the primary embryos in a development medium. Surprisingly, this is a convenient and efficient source of tissue for forming secondary embryos for, at least, plants of Cannabis sativa L. species.

Providing the secondary embryos may further comprise placing the tissue, or one or more pieces obtained by cutting the tissue, in an induction medium, being the aforementioned induction medium or a further induction medium that comprises or consists of the plant cell culture medium in accordance with embodiments of the second aspect of the present invention, and exposing the tissue to light, e.g. for a period sufficient to obtain secondary embryos. Optionally, the secondary embryos may be transferred into a development medium and cultured with exposure to light to further expand the secondary embryos.

Incubation may be continued for a period sufficient to allow maturation, pre-germination and optionally also germination of the embryos, e.g. the secondary embryos. The photoautotrophic step may be followed by a plant regeneration step, and/or a plant growth cultivation step. Plants, plants bearing flowers, and plant materials may thus be obtained by a method in accordance with embodiments of the present invention, e.g. after the plant regeneration and a conventional plant growth cultivation step, e.g. a nurturing step.

The micropropagation method may comprise transferring and culturing the primary and/or secondary embryos, preferably at least the secondary embryos, in a medium for maturation and pre-germination of the direct primary and/or secondary embryos into plants, e.g. for a period sufficient to allow maturation, pre-germination and optionally also germination of the embryos in the medium, The medium for maturation and pre-germination may be a medium in accordance with embodiments of the second aspect of the present invention. The medium for maturation and pre-germination may comprise an Amino Acid Stock 1000×, e.g. at a preferred concentration of about 2 ml/L, which includes L-Lysine 91.3 mg, L-Leucine 65.6 mg, L-Tryptophan 102.1 mg, Arginine 87.1 mg, and Glycine 37.52 mg.

As an example, the process step of forming primary embryos, forming secondary embryos and maturation and pre-germination may be carried out within a period in the range of 5 to 9 weeks, for example in the range of 5 to 7 weeks, e.g. particularly for the exemplary application of Cannabis Sativa L. propagation. Suitably, the medium may be changed, e.g. refreshed, on a number of occasions during this treatment, for example three to eight times during the step of maturation and pre-germination.

The micropropagation method may comprise developing plantlets from the pre-germinated or germinated embryos, e.g. in a step of germination and conversion of the embryos into plants. This step may be carried out in a germination and conversion medium, e.g. comprising a medium in accordance with embodiments of the second aspect of the present invention.

For example, the pre-germinated or germinated secondary embryos may be developed into plantlets using conventional methods. For example, the in-vitro generated materials may be transplanted in a nursery for acclimatization in a culture substrate, which may comprise a mixture of components such as perlite, coconut peat, soil, etc. for example. Subsequently, the plants may be transplanted in the field and grown into Cannabis sativa L. plants.

For example, the process of forming primary embryos, secondary embryos, maturation, pre-germination and initial plant development, e.g. from the initial in-vitro induction to the greenhouse, may be carried out, for the exemplary Cannabis sativa L. species, in a period ranging from 8 weeks to one year, preferably from 20 to 28 weeks.

The plant cell culture medium or media used in the step of providing primary and/or secondary embryos and/or the medium for maturation and pre-germination and/or the medium for germination and conversion of embryos into plants may be in liquid form. Such medium in liquid form may be held, in use, in any suitable container, although preferably a photobioreactor is used in a method in accordance with embodiments of the present invention. Incubation may be effected at a temperature in the range of 23° C. to 29° C., preferably in the range of 25° C. to 26° C. Maturation, pre-germination and germination steps may be carried out with exposure to light. Exposure of light may comprise exposure to photo-synthetically active radiation (PAR), e.g. in the wavelength range of 400 nm to 700 nm, e.g. at a photosynthetic photon flux in the range of 100 to 200 $\mu mol\ m^{-2}\ s^{-1}$. For example, a photobioreactor, such as a bubble photobioreactor or an air-lift photobioreactor may be used. The use of any other bioreactor via continuous and/or temporary immersion, are also within the scope of this invention.

Furthermore, by implementing maturation, pre-germination, germination and/or conversion of embryos into plants in a photobioreactor, the plant propagation process can be carried out with great efficiency and in a simple manner. The use of such bioreactors makes the process amenable to automation and provides for cost and labor savings due to factors such as the reduced need for manual steps and the use of gelling agents.

It is an advantage of a photoautotrophic approach that the culture period may be significantly reduced, e.g. by as much as 50% compared to conventional photomixotrophic systems.

In indirect somatic embryogenesis, cells derived from competent source tissue are cultured to form an undifferentiated mass of cells, called a callus. However, direct embryogenesis offers a few advantages over indirect somatic embryogenesis, such as a shorter period needed for obtaining direct somatic embryos, the reduction on the culture time that might decrease the frequency of somaclonal variations and the ability of minimizing or eliminating the risk of producing chimeric plants. Direct somatic embryogenesis is a morphological event in which somatic embryos originate directly from the plant's tissue matrix, without the formation of callus as an intermediate stage. This is the key difference between direct and indirect somatic embryogenesis: indirect somatic embryogenesis requires callus formation. Another difference between these types of regeneration is the response to the action of growth regulators. Whereas direct somatic embryogenesis is generally characterized by the cultivation of a single culture medium with the addition of just a cytokinin or another stressor agent, indirect somatic embryogenesis is generally characterized as requiring a high auxin concentration or specific ratios of auxin/cytokinin for callus formation in an initial culture medium. After callus is formed, another medium having no auxin or a lower concentration of auxin is used during subsequent transfers, as compared to the medium used for embryogenic callus induction. Indirect somatic embryogenesis requires a carefully timed and quantitatively controlled process that is tuned to the specific plant species.

Thus, in direct somatic embryogenesis, embryos can be produced without the formation of any embryogenic callus, thereby providing a way of obtaining a large number of normal embryos in a short time, as compared with indirect somatic embryogenesis procedures. In specific embodiments of the present invention, the plant used to initiate somatic embryogenesis is *Cannabis sativa*, preferably *Cannabis sativa* L. By using direct somatic embryogenesis in a method in accordance with embodiments of the present invention for forming primary and secondary embryos, problems associated with the use of undifferentiated callus material can be avoided.

By such method, one can not only increase the growth of in vitro plantlets, but also minimize the risk of loss due to microbial contamination, reduce production costs, improve the physiological characteristics of the plantlets and enable better acclimatization ex vitro. The ability of somatic embryos to grow photoautotrophically enables automation, which can lead to a reduction of production costs. Moreover, photoautotrophic growth can improve the quality of somatic embryos and possibly shorten and simplify the germination and plantlet development procedure.

Developmental and operational stages for conventional micropropagation are generally classified into four or five stages. For photoautotrophic micropropagation, the number of classified stages may be less than in conventional photomixotrophic micropropagation, since multiplication and rooting stages may be combined into a single stage in photoautotrophic micropropagation by reproducing photosynthetically active, leafy nodal cuttings to be used as explants. Therefore, only the introduction/initiation stage of the culture (stage I) may be under photoheterotrophic/photomixotrophic conditions where virus (or pathogen) free cultures are established to induce somatic embryo. Once the chlorophyllous organs, able to conduct photosynthesis, are developed, the cultures are ready to move on to photoautotrophic micropropagation conditions. The acclimatization stage may be eliminated, such that a photoautotrophic micropropagation system is formed that may exclusively consist of two stages, initiation (stage I) and multiplication/rooting (stage II), while a conventional photomixotrophic micropropagation requires four stages, initiation (stage I), multiplication (stage II), rooting/preparation (stage III), and acclimatization (stage IV).

Hereinbelow, examples and experimental results are presented for illustrating aspects and applications of embodiments of the present invention. It shall be understood that such examples and/or experimental results are merely illustrative and not intended as limiting the present invention.

The general application of somatic embryogenesis requires the development of uniform, high efficiency regeneration systems which can produce plants that perform as seed-derived plants. The development of protocols to establish embryogenic cultures using more readily available material would alleviate many of the problems associated with immature embryo explants. By way of example, the present disclosure describes a simple and efficient protocol that uses cotyledons from mature, dry, seeds from which somatic embryos can be induced at a high frequency. Mature seeds of *Cannabis sativa* L. (USO-31) were obtained from Agrolitpa, Kerava, Lithuania. The seeds were surface sterilized with 0.1% (W/V) aqueous mercuric chloride solution for 8 min and thoroughly washed (3 times) with sterile distilled water several times. Then, the seeds were divided into two halves and embryogenic axes were removed from the cotyledons. for induction of somatic embryogenesis, deembryonated cotyledons (without any pre-existing meristem) were placed on a modified photoautotrophic MS basal medium, optimized in previous experiments, supplemented with 10 mg $L^{-1}$ citric acid, and 1 ml/L NAA, and 6 g $L^{-1}$ Floralite (Nisshinbo Industries Inc., Tokyo) for the control medium+recombinant Arg9-NLS-BBM fusion protein, in accordance with embodiments of the present invention, for the other medium. A composition of an optimum, or at least considerably suitable, medium for induction of somatic embryogenesis in *Cannabis sativa* L. is provided in the table TABLE A presented hereinabove.

A second group of Deembryonated cotyledons (also without any pre-existing meristem) were placed on the same optimized photoautotrophic MS basal medium, only this time with the addition of the recombinant Arg-NLS-BBM fusion protein, in accordance with embodiments of the present invention, at various concentrations, ranging from 0.5 mg/L, 1.0 mg/L, 1.5 mg/L, 2.0 mg/L, 2.5 mg/L, and 3.0 ml/L, respectively to test the increase of direct embryogenesis induction rate of *Cannabis sativa* L. against the control medium. According to the sequence of *Arabidopsis thaliana* gene BBM_ARATH (see UniProtKB reference hereinabove), Poly-Arg and NLS, the artificial sequence of Arg9-NLS-BBM was synthesized. The fusion construct was transiently over-expressed in *Nicotiana benthamiana* plants and the recombinant protein was extracted and purified. After the purified protein was sterilized by passing filter membrane, it was added into the cell culture media.

All culture media being used are modified autotrophic MS (Murashige & Skoog 1962) basal medium, in which $NH_4NO_3$ was replaced by $NaNO_3$. The pH was adjusted to 5.7±0.1 and the medium was sterilized by autoclaving at 121° C. with 1.04 kg $cm^{-2}$ pressure for 20 min. Routinely, 15 ml of liquid medium with 0.6% (W/V) Florialite was dispensed into culture tubes (25' 150 mm) and plugged with non-absorbent cotton wrapped in one layer of cheese-cloth.

The cultures were incubated in a growth room (Conviron, Germany) at 25±2° C. under a 24-h photoperiod provided by a photo-synthetically active radiation (PAR) source between 400-700 nm, in a photosynthetic photon flux between 100- and 200 µmol $m^{-2}$ $s^{-1}$.

When somatic embryos were observed using a stereomicroscope (Laxco™ LMS-Z300 Series Stereo Zoom Microscope System, Thermo Scientific, Belgium), embryogenic masses with proliferating embryos were transferred on to fresh embryo maturation medium which consisted of aforementioned optimized photoautotrophic MS basal medium with the addition Amino Acid Stock 1000× at 2 ml/L (L-Lysine 91.3 mg, L-Leucine 65.6 mg, L-Tryptophan 102.1 mg, Arginine 87.1 mg, and Glycine 37.52 mg) with BAP (2.22 m M) as the control medium and with the addition of recombinant Arg9-NLS-BBM fusion protein in the other medium, according to the composition in TABLE B hereinabove.

For germination, somatic embryos were transferred from embryo maturation medium onto embryo germination medium, which consisted of half-strength of the same optimized photoautotrophic MS basal medium without any growth regulators in both medium but still containing the recombinant Arg9-NLS-BBM fusion protein in the other medium, according to the composition in TABLE C hereinbelow.

TABLE C

| Micro-elements | Concentration [mg/l] |
|---|---|
| $CoCl_2 \cdot 6H_2O$ | 0.013 |
| $CuSO_4 \cdot 5H_2O$ | 0.013 |
| FeNaEDTA | 18.35 |
| $H_3BO_3$ | 3.10 |
| KI | 0.42 |
| $MnSO_4 \cdot H_2O$ | 8.45 |
| $Na_2MoO_4 \cdot 2H_2O$ | 0.13 |
| $ZnSO_4 \cdot 7H_2O$ | 4.30 |

| | Concentration [mg/L] |
|---|---|
| Macro-elements | |
| $CaCl_2$ | 166.01 |
| $KH_2PO_4$ | 85.00 |
| $KNO_3$ | 950.00 |
| $MgSO_4$ | 90.27 |
| $NaNO_3$ | 875.50 |
| Additions | |
| $C_6H_8O_7$ | 5.0 |
| Amino Acid Stock 1000X | 1.0 |
| Arg9-NLS-BBM | 2.0 |

In order to achieve further shoot elongation and full root development from germinated somatic embryos, plantlets were transferred to optimized photoautotrophic MS basal medium containing BAP and Meta-Topolin (MT) in the control medium and BAP+MT+recombinant Arg9-NLS-BBM fusion protein in the other medium, according to the composition in TABLE D hereinbelow, both incubated in a growth room at 25±2° C. under a 24-h photoperiod provided by a photo-synthetically active radiation (PAR) source between 400-700 nm, in a photosynthetic photon flux between 100- and 200 µmol m$^{-2}$ s$^{-1}$.

TABLE D

| Micro-elements | Concentration [mg/l] |
|---|---|
| $CoCl_2 \cdot 6H_2O$ | 0.025 |
| $CuSO_4 \cdot 5H_2O$ | 0.025 |
| FeNaEDTA | 36.70 |
| $H_3BO_3$ | 6.20 |
| KI | 0.83 |
| $MnSO_4 \cdot H_2O$ | 16.90 |
| $Na_2MoO_4 \cdot 2H_2O$ | 0.25 |
| $ZnSO_4 \cdot 7H_2O$ | 8.60 |

| | Concentration [mg/L] |
|---|---|
| Macro-elements | |
| $CaCl_2$ | 332.02 |
| $KH_2PO_4$ | 170.00 |
| $KNO_3$ | 1900.00 |
| $MgSO_4$ | 180.54 |
| $NaNO_3$ | 1721.00 |
| Additions | |
| $C_6H_8O_7$ | 10.0 |
| $C_{12}H_{11}N_5$ (BAP) | 0.75 |
| $C_{12}H_{11}N_5O$ (MT) | 0.25 |
| Arg9-NLS-BBM | 2.0 |

A minimum 35 explants were cultured for each treatment combination and each experiment was repeated thrice. The data pertaining to percentage of embryogenesis and mean number of embryos per culture were calculated and statistically analysed by the Duncan's New Multiple Range Test. Among the treatments, the average figures followed by similar letter are not significantly different at the 1% level.

For histological studies, the embryos at various stages of embryogenesis were fixed in FAA (formaldehyde-acetic acid-ethanol) for 24 h. Tissues were dehydrated by transferring embryos through an ethanol-xylol series and then were infiltrated and embedded in paraffin. Tissues were sectioned to 6 mm with a microtome, mounted on glass slides, and stained with safranin.

Photographs were taken under Nikon light microscope. Direct somatic embryogenesis was observed from mature cotyledon explants within 28 days of culture initiation. Cotyledons enlarged after 7 days of culture initiation on induction medium. Greenish rounded structures appeared on the cut end of the explants within 2 weeks of culture on optimized photoautotrophic MS basal medium augmented with varying concentrations of recombinant Arg9-NLS-BBM fusion protein. These protuberances are referred to as embryos. The frequency of embryogenesis increased with the concentration of recombinant Arg9-NLS-BBM fusion protein from 0.5 mg/L up to 2.0 mg/L, then decreased with further increase in the concentration up to 3.0 ml/L. Among the various concentrations tested, recombinant Arg9-NLS-BBM fusion protein at 2 ml/L was the optimum concentration for high frequency of embryogenesis as well as the maximum number of somatic embryos. A maximum embryogenesis obtained was 88.2% with 2 ml/L which was statistically significant at 1% level.

Furthermore, it was found that the embryogenic-induced rate of Cannabis sativa L. in the media containing the recombinant foreign protein was significantly higher than those on the control media. This indicated that after the recombinant protein touched with the explant cells, poly-Arg transduction domain can lead the followed amino acids pass through the cell membrane. The NLS can lead the followed protein to enter the nucleus. In the nucleus, the transcription factor BBM can bind with the target DNA sequence and can significantly induce the embryogenesis response rate of Cannabis sativa L. somatic cells.

Somatic embryos which developed within 4 weeks from 88.2% of the embryogenic masses were transferred to maturation medium. Embryos of various shapes and stages were visible in the clusters, indicating that the process of embryogenesis was asynchronous. Cotyledonary embryos were also noticed after 4 weeks of culture on the same maturation medium. Most such embryos were morphologically normal, and green in appearance with a distinct hypocotyl region and normal cotyledons. Many embryos underwent further development by elongation of the hypocotyl and cotyledon expansion producing later stage embryos. These embryos frequently exhibited secondary embryogenesis, unless transferred to embryo germination medium, with early stage embryos being produced from the hypocotyl and cotyledons. During somatic embryogenesis from immature leaflets of Cannabis sativa L., globular, heart and torpedo stages were not clearly delimited.

Figure 2:
Figure 3:
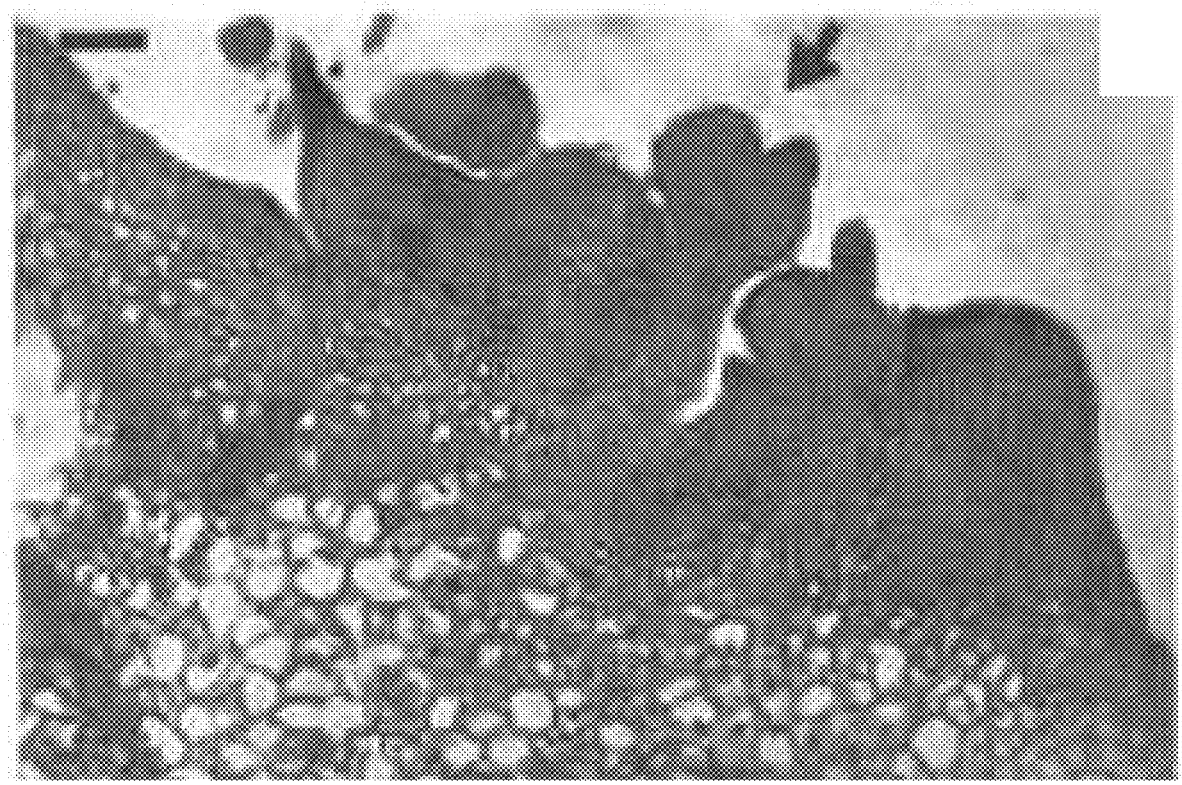
Figure 4:
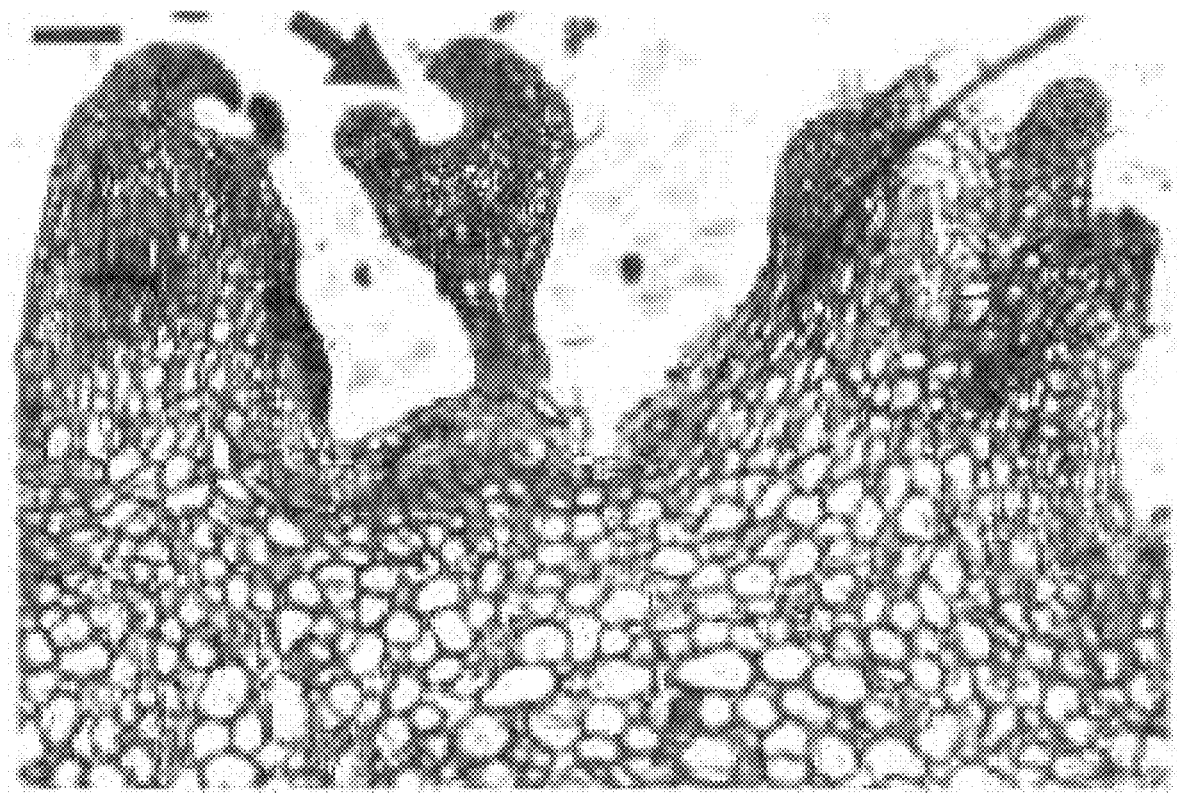

More than 92% plantlets were produced out of the total embryos cultured on germination medium. The average plant conversion was 86%. Histology of somatic embryo-producing regions of cotyledons confirmed that the induction of the development process was embryogenic and not organogenic in nature. Light microscopic observations of embryogenic mass revealed the presence of nodular structures containing cytoplasmic cells at the central region. Development of somatic embryos appeared to progress through typical globular-, heart-, torpedo-shaped and cotyledonary stage embryo development. The first sign of embryogenesis was marked by the appearance of globular structures that were attached to the surface of the explant by a distinct stalk, as shown in FIG. 1. The heart-stage embryo, see FIG. 2, which was bilaterally symmetrical also showed a broad suspensor-like stalk. Some of the structures also had vascular tissue with unipolar meristems which ultimately developed into roots. The densely stained meristematic area was often completely surrounded by parenchymatous tissue. At this stage, development of clear bipolar embryos with organized shoot and root portion was observed, see FIG. 3. The cotyledonary-stage embryos showed the presence of two prominent cotyledons, see FIG. 4.

In the present study, cotyledons were used to obtain a high frequency of somatic embryogenesis, and cotyledons from mature seeds are a convenient, accessible and efficient explant for somatic embryogenesis in *Cannabis sativa* L. Altogether, in our findings, we found that after the recombinant Arg9-NLS-BBM fusion protein was added into the medium, the embryogenic-induced rate of *Cannabis sativa* L. can be improved significantly by as much as 19% versus control. According to our knowledge, this is also the first paper reported that *Cannabis sativa* L. direct embryogenesis can be induced by adding artificial plant transcription protein into photoautotrophic culturing medium. Considering the advent of photoautotrophic micropropagation and the economic importance of *Cannabis sativa* L. and other *Cannabis* Species, there is a high demand for development of less labor intensive, automated tissue culture procedure leaning to development of hardened plants which will not require acclimatization. A major advantage of the present invention is drastic reduction in contamination due to non-inclusion of sugar in the medium and use of non-agar supporting matrix. This further indicates reduction in stringency of culture process and relaxed aseptic environment. Furthermore, the addition of plant transcription factors can be added to significantly increase embryogenesis rate and conversion to plantlets. The present invention allows for use of larger culture vessels which indirectly imply robotization in the overall process and scope of higher throughput in commercial adaptation.

Results of the experiments discussed hereinabove are summarized in the table hereinbelow. A comparison is presented of the photoautotrophic medium control versus media in which various amounts of the recombinant Arg9-NLS-BBM fusion protein were added. The 'overall quality' metric is obtained by the gestalt rating of Niedz et al, in which the scores of 1, 2 and 3 correspond respectively to a poor, intermediate and good overall quality.

|  | Control medium | +0.5 mg/l Arg8-NLS-BBM | +1.0 mg/l Arg8-NLS-BBM | +1.5 mg/l Arg8-NLS-BBM | +2.0 mg/l Arg8-NLS-BBM | +2.5 mg/l Arg8-NLS-BBM | +3.0 mg/l Arg8-NLS-BBM |
|---|---|---|---|---|---|---|---|
| Embryo induction | $242 \times 8^4$ | $281 \times 8^4$ | $316 \times 8^4$ | $378 \times 8^4$ | $513 \times 8^4$ | $469 \times 8^4$ | $395 \times 8^4$ |
| Embryo maturation | $186 \times 8^4$ | $266 \times 8^4$ | $278 \times 8^4$ | $342 \times 8^4$ | $497 \times 8^4$ | $424 \times 8^4$ | $361 \times 8^4$ |
| Embryo germination | $141 \times 8^4$ | $234 \times 8^4$ | $251 \times 8^4$ | $309 \times 8^4$ | $482 \times 8^4$ | $391 \times 8^4$ | $322 \times 8^4$ |
| Overall quality | 1 | 2 | 2 | 2 | 3 | 3 | 2 |

The invention claimed is:

1. A recombinant protein for use in a liquid culture medium for photo-autotrophic micropropagation of *Cannabis sativa* L., the recombinant protein comprising:

an Arabinogalactan protein and/or a plant transcription factor associated with plant growth and development, and a cell penetrating peptide sequence and a nuclear localization signal, wherein said nuclear localization signal is encoded by the peptide sequence SEQ ID NO 1, wherein said cell penetrating peptide sequence comprising a sequence of 7 to 25 arginines forming a poly-arginine transduction domain, wherein said plant transcription factor comprises AP2-like ethylene-responsive transcription factor BBM from *Arabidopsis thaliana*, or an analog to said AP2-like ethylene-responsive transcription factor BBM from *Arabidopsis thaliana*, wherein said analog is codon-optimized for a host species.

2. The recombinant protein of claim 1, wherein said plant transcription factor comprises one or more of: Baby Boom, BBM, Leafy Cotyledon, LEC, Wuschel, WUS, RWP-RK Domain-Containing 4, RKD4, Wound Induced Dedifferentiation 1, WIND1, and Plethora2, PLT2.

3. The recombinant protein of claim 1, wherein said host species is *Nicotiana benthamiana*.

4. The recombinant protein of claim 1, wherein said recombinant protein is encoded by the nucleotide sequence SEQ ID NO 2.

5. A plant cell culture medium comprising the recombinant protein of claim 1.

6. The plant cell culture medium of claim 5, comprising the recombinant protein in a concentration in the range of 0.05 mg/L to 5 mg/L.

7. The plant cell culture medium of claim 5, further comprising salts and/or vitamins.

8. The plant cell culture medium of claim 5, comprising one or more of the following: 6-benzylaminpurine, Ethephon, Kinetin, Putrescine, Spermidine, Hydrogen Peroxide, 6-(Y,Y-dimethylallylamino) purine, Gibberellic Acid or Gibberellin, and Naphthaleneacetic Acid.

9. The plant cell culture medium of claim 5, wherein said medium is a liquid culture medium for photo-autotrophic micropropagation.

10. A method for micropropagation of *Cannabis sativa* L., the method comprising:
    obtaining explant material from a *Cannabis sativa* L. plant,
    providing primary and/or secondary embryos by inducing embryogenesis in the explant material in the plant cell culture medium of claim 5.

11. The method of claim 10, wherein providing primary and/or secondary embryos comprises a photoautotrophic method in which the explant material is exposed to light for stimulating direct somatic embryogenesis.

12. The method of claim 11, wherein said exposure to light comprises the exposure to light from a photo-synthetically active radiation (PAR) source, in the wavelength range of 400 nm to 700 nm, and at a photosynthetic photon flux between 100 and 200 µmol m-2 s-1.

13. The recombinant protein of claim 1, wherein the recombinant protein comprises, or consists of, a fusion of the 9 arginine residues (Arg9), the nuclear localization signal or sequence is encoded by the peptide sequence SEQ ID NO: 1 (NLS), and the AP2-like ethylene-responsive transcription factor BBM from *Arabidopsis thaliana* or an analog wherein the host species is *Nicotiana benthamiana*.

* * * * *

SEQUENCE LISTING

```
<160> NUMBER OF SEQ ID NOS: 3

<210> SEQ ID NO 1
<211> LENGTH: 20
<212> TYPE: PRT
<213> ORGANISM: Artificial
<220> FEATURE:
<223> OTHER INFORMATION: nuclear localization signal

<400> SEQUENCE: 1

Arg Arg Lys Pro Ser Trp Arg Glu Arg Glu Asn Asn Arg Arg Arg Glu
1               5                   10                  15

Arg Arg Arg Arg
            20

<210> SEQ ID NO 2
<211> LENGTH: 1839
<212> TYPE: DNA
<213> ORGANISM: artificial
<220> FEATURE:
<223> OTHER INFORMATION: recombinant protein coding sequence
      codon-optimized for Nicotiana

<400> SEQUENCE: 2
aggagaagac gtcggaggag aaggagacgt agaaagcctt cttggcggga aagagaaaac      60
aaccgtagga gggaaagaag acgaaggatg aattctatga caactggct gggcttttcc     120 ttatctccgc atgatcagaa tcatcataga actgatgtcg attcttcaac taccaggact    180
```

```
gctgtggacg tcgctggtgg atactgcttc gaccttgctg caccgagcga cgaatcatca    240
gctgttcaga ccagtttcct ctcaccattt ggagtaactt tggaggcatt cacgcgtgat    300
aataattctc attctcggga ttgggatata aatggtggtg cttgtaataa catcaataat    360
aatgagcaga atggtccgaa attggagaat tttctgggaa gaacaaccac catttacaac    420
acaaacgaaa cagtagtgga tggcaatgga gattgcggtg gaggtgatgg aggtggcggt    480
ggttcacttg gattgtctat gataaagaca tggttgagta accattctgt tgcaaatgct    540
aatcatcagg ataacgggaa tggagcaagg ggattgagtt tatcaatgaa ctcttctaca    600
agcgacagta acaattataa caataatgat gatgttgttc aagaaaaaac aatagtcgat    660
gttgttgaaa caactccaaa gaagacaatt gaatcctttg gacaaagaac tagcatatac    720
agaggagtga ctaggcaccg atggacaggg cgttatgagg cacatctttg ggataattct    780
tgtaaaagag aaggacagac caggaaggga cgacaggtat acctcggtgg ttatgacaag    840
gaggagaaag ctgctagggc ttatgattta gcagctctca agtattgggg cacaacaacc    900
acaacaaatt tccctctttc tgagtatgaa aagaagtcg aagagatgaa gcacatgaca    960
aggcaggaat acgtagcttc tcttagaaga aagtctagtg gcttttcacg gggcgctagt   1020
atatacagag gtgttactag gcatcaccaa cacggacgat ggcaggcaag aattggtcga   1080
gttgctggaa ataaagacct gtacctggga actttcggga cccaagagga agccgcagag   1140
gcttacgata ttgctgctat taaattcagg ggattatcag ccgtcactaa ctttgatatg   1200
aataggtata atgttaaggc tattcttgaa tctccttcat taccaattgg gagtagcgcc   1260
aagagattga aggatgtaaa caatccggta cctgctatga tgattagcaa taacgtaagc   1320
gagtcagcta acaatgtttc tggatggcaa aatacggctt tccagcacca tcagggtatg   1380
gacctttcat tgctgcaaca gcagcaggaa aggtatgtgg ggtactacaa tggtggtaat   1440
ttgagtacag agagcaccag agtttgtttt aagcaggaag aagagcaaca acatttttg    1500 aggaattctc cttcacacat gaccaatgtt gatcaccatt ctagtacctc agatgattct   1560
gtaacagtct gtggaaatgt cgtctcatac ggtggatacc agggattcgc tattccagtt   1620
ggcacaagtg tcaactatga tccatttaca gctgcagaga tcgcctataa cgcaaggaac   1680
cactattatt acgcacaaca tcaacaacaa caacagattc aacagtcccc gggtggagac   1740
ttcccagttg caattagcaa caatcacagc tctaatatgt actttcatgg agaaggcggt   1800
ggtgagggtg cacctacctt ttctgtgtgg aacgatacc                           1839
```

<210> SEQ ID NO 3
<211> LENGTH: 9
<212> TYPE: PRT
<213> ORGANISM: artificial
<220> FEATURE:
<223> OTHER INFORMATION: poly-arginine transduction domain

<400> SEQUENCE: 3

Arg Arg Arg Arg Arg Arg Arg Arg Arg
1               5